(12) United States Patent
Williams et al.

(10) Patent No.: US 9,164,583 B2
(45) Date of Patent: Oct. 20, 2015

(54) METHOD AND APPARATUS FOR GAZE POINT MAPPING

(75) Inventors: Denis Williams, Berlin (DE); Jan Hoffman, Berlin (DE)

(73) Assignee: SENSO-MOTORIC INSTRUMENTS GESELLSCHAFT FUR INNOVATIVE SENSORIK MBH, Berlin (DE)

( * ) Notice: Subject to any disclaimer, the term of this patent is extended or adjusted under 35 U.S.C. 154(b) by 81 days.

(21) Appl. No.: 14/005,657

(22) PCT Filed: Mar. 16, 2012

(86) PCT No.: PCT/EP2012/054691
§ 371 (c)(1),
(2), (4) Date: Sep. 17, 2013

(87) PCT Pub. No.: WO2012/126844
PCT Pub. Date: Sep. 27, 2012

(65) Prior Publication Data
US 2014/0003738 A1     Jan. 2, 2014

(30) Foreign Application Priority Data
Mar. 18, 2011    (EP) .................................... 11158922

(51) Int. Cl.
| | |
|---|---|
| *G06K 9/36* | (2006.01) |
| *G06K 9/00* | (2006.01) |
| *G06F 3/01* | (2006.01) |
| *A61B 3/113* | (2006.01) |
| *G06T 7/00* | (2006.01) |
| *G06T 5/50* | (2006.01) |
| *G06K 9/46* | (2006.01) |

(52) U.S. Cl.
CPC ................ *G06F 3/013* (2013.01); *A61B 3/113* (2013.01); *G06K 9/0061* (2013.01); *G06K 9/4671* (2013.01); *G06T 5/50* (2013.01); *G06T 7/003* (2013.01)

(58) Field of Classification Search
CPC ............ G06F 3/013; G06T 5/50; G06T 7/003; A61B 3/313; G06K 9/00335; G06K 9/00604; G06K 9/0061
USPC .................................. 382/103, 190, 276, 282
See application file for complete search history.

(56) References Cited

U.S. PATENT DOCUMENTS

| | | | |
|---|---|---|---|
| 5,260,734 A * | 11/1993 | Shindo ............................ | 396/51 |
| 5,708,862 A * | 1/1998 | Tsunekawa et al. ............ | 396/51 |
| 5,912,721 A * | 6/1999 | Yamaguchi et al. ........... | 351/210 |
| 7,736,000 B2 * | 6/2010 | Enriquez et al. .............. | 351/210 |
| 8,408,706 B2 * | 4/2013 | Yahav ........................... | 351/210 |

* cited by examiner

*Primary Examiner* — Kanjibhai Patel
(74) *Attorney, Agent, or Firm* — Huffman Law Group, PC

(57) ABSTRACT

An apparatus for mapping a gaze point of a subject on a scene image to a gaze point in a reference image, wherein said scene image and said reference image have been taken by a camera from a different position, said apparatus comprising: A module for executing a feature detection algorithm on said reference image to identify a plurality of characteristic features and their locations in said reference image; a module for executing said feature detection algorithm on said scene image to re-identify said plurality of characteristic features and their locations in said scene image; a module for determining a point transfer mapping that transforms point positions between said scene image and said reference image based on the locations of said plurality of characteristic features detected in said reference image and said scene image; a module for using said point transfer mapping to map a gaze point which has been determined in said scene image to its corresponding point in said reference image.

15 Claims, 2 Drawing Sheets

METHOD AND APPARATUS FOR GAZE POINT MAPPING

FIELD OF THE INVENTION

The present invention relates to a method and an apparatus for gaze point mapping, in particular for mapping a gaze direction of a subject to a gaze point in a scene.

BACKGROUND OF THE INVENTION

The problem to be solved is finding the point or the object or more specific the part of an object's surface that a (possibly moving) person gazes at. There are existing solutions to this problem described below which can be split into separate parts.

At first the gaze direction of the person (or a representation thereof like a pupil/CR combination, cornea center and pupil/limbus etc.) is to be found.

This gaze direction is mapped to an image of the scene captured by a head-mounted scene camera or a scene camera at any fixed location. The head-mounted scene camera is fixed with respect to the eye, and therefore such a mapping can be performed, once a corresponding calibration has been executed.

The next step is to map the gaze point in the scene image as captured by the head-mounted camera, which can change due to the movement of the subject, to a point in a (stable) reference image which does not move and which corresponds to a "real world" object.

For determining the gaze direction eye trackers can be used. Eye Trackers observe features of the eye like the pupil, the limbus, blood vessels on the sclera or reflections of light sources (corneal reflections) in order to calculate the direction of the gaze.

Any kind of eye tracker can be used if it allows mapping the gaze direction into images of a head-mounted scene camera.

If the head of the subject does not move, once the calibration is done the determination of the gaze direction directly gives the gaze point on the reference image. The calibration in this special case when the head does not move gives the mapping of a gaze direction from a point in the scene image to a point in the reference image, because the scene image and the reference image are identical as the head-mounted camera does not move but has a fixed location with respect to the reference image.

If, however, the head and the eye move, it becomes more complicated to determine the gaze point in a reference image which does not move based on the detection of the gaze direction with respect to a certain scene image as taken by the head-mounted camera after the head has moved, as the scene image then is not anymore identical with the reference image which was used for calibrating the gaze direction with respect to the corresponding gaze point in the reference image.

One possible approach of determining the point gazed at is to intersect the gaze direction with a virtual scene plane defined relative to the eye tracker. WO 2010/083853 A1 discloses to use active IR markers for that purpose, which are fixed at certain locations, e.g. attached to a bookshelf. The locations of these markers are first detected with respect to a "test scene" which acts as a "reference" image obtained by the head-mounted camera, by use of two orthogonal IR line detectors which detect the two orthogonal angles by detecting the maximum intensity of the two line sensors. The detected angles of an IR source correspond to its location in the reference image. Then the angles of the markers are detected for a later detected scene taken by the head-mounted camera from a different position, thereby detecting the location of the IR sources in the later scene image. Then there is determined the "perspective projection", which is the mapping that transforms the locations of the IR sources as detected in an image taken later (a scene image), when the head-mounted camera is at a different location, to the locations of the IR light sources in the test image (or reference image). With this transformation a gaze point as determined later for the scene image can also be transformed into the corresponding (actual) gaze point in the test image.

The mapping of the gaze point from the actual "scene image" to a stable reference image which is time invariant becomes possible by defining the plane on which the gaze point is mapped in relation to scene stable markers instead of to the eye tracker (ET). This way the plane of the reference image becomes stable over time and gazes of other participants can also be mapped onto it so that the gaze point information can be aggregated over time as well as over participants like it could only be done before with eye trackers located at a fixed position.

For that purpose the prior art as disclosed in WO 2010/083853 A1 uses IR sources as artificial markers the locations of which can be detected by orthogonal IR line detectors to detect the angles of maximum emission.

The usage of using IR sources as markers for determining the transform of the gaze point from a scene image to a reference image is complicated and inconvenient. It requires artificial IR light sources to be mounted, and it makes it necessary to have an additional IR detector comprising two orthogonal line sensors. It is therefore desirable to provide an approach which can determine a gaze point mapping even if the head-mounted scene camera moves without such external markers.

SUMMARY OF THE INVENTION

According to one embodiment there is provided an apparatus for mapping a gaze point of a subject on a scene image to a gaze point in a reference image, wherein said scene image and said reference image have been taken by a camera from a different position, said apparatus comprising:

A module for executing a feature detection algorithm on said reference image to identify a plurality of characteristic features and their locations in said reference image;

a module for executing said feature detection algorithm on said scene image to re-identify said plurality of characteristic features and their locations in said scene image;

a module for determining a point transfer mapping that transforms point positions between said scene image and said reference image based on the locations of said plurality of characteristic features detected in said reference image and said scene image;

a module for using said point transfer mapping to map a gaze point which has been determined in said scene image to its corresponding point in said reference image.

This enables the implementation of gaze point mapping which does not need any artificial IR sources and IR detectors. It can operate on normal and unamended images of natural scenes taken by normal CCD-cameras operating in the visible frequency range.

According to one embodiment said point transfer mapping is a planar homography which is estimated from the features in the reference image and scene image and transfers point positions via a virtual transfer plane in the world scene from said scene image to said reference image.

This is a particularly suitable implementation of the point transfer mapping.

According to one embodiment the apparatus further comprises:

A module for determining one or more regions of interest in said reference image within which said feature detection algorithm is executed to detect and locate said characteristic features therein.

This enables the selection of suitable regions for the feature detection algorithm. This enhances the efficiency of the feature detection algorithm by enabling the user to select regions with particularly characteristic features.

According to one embodiment said feature detection algorithm for detecting said plurality of characteristic features in said scene image and for detecting and re-identifying said characteristic features in said scene image comprises one of the following:

A scale invariant feature transform algorithm;

a speeded up robust features algorithm.

These are particularly suitable implementations of the feature detection and re-identification algorithms.

According to one embodiment the apparatus further comprises:

A module for mapping the gaze directions from different persons and/or different times to the corresponding gaze points in the reference image and for recording the mapped gaze points over time, possibly also for different users.

This enables the aggregation and accumulation of gaze data over time, possibly even for different users.

According to one embodiment the apparatus further comprises:

A module displaying said gaze point which has been mapped from said scene image to said reference image in said reference image to visualize said gaze point, possibly as its location evolves over time.

This enables the visualization of the gaze point which has been mapped into the reference image, possibly even over time.

According to one embodiment the apparatus further comprises:

A module for visualizing said gaze point which has been mapped from said scene image to said reference image in a visualization image different from said reference image, said module comprising:

a module for determining a point transfer mapping for transferring a point from said reference image to said visualization image;

a module for using said point transfer mapping to map said gaze point from said reference image to its corresponding point in said visualization image; and a module for displaying said gaze point on said corresponding point in said visualization image.

This enables the mapping of the gaze point into and the visualization in an image different from said reference image.

According to one embodiment the apparatus further comprises:

A module for determining said point transfer mapping based on characteristic features which have been detected in said reference image by a feature detection algorithm and which have been detected and re-identified in said visualization image by said feature detection algorithm.

This is a suitable implementation of the point transfer mapping for the visualization.

According to one embodiment said visualization image is one of the following:

an image selected from scene images taken from different positions;

an image generated by stitching two or more of the scene images taken from different positions;

a geometrically modified image of the scene;

an image of the scene from which distortions have been removed an image taken at a time different from the actual measurement of the gaze points;

an image having a higher resolution than said reference image;

a cartoon or a sketch;

a stylized drawing a handmade drawing.

These are suitable implementations for visualization images different from the reference image.

According to one embodiment the apparatus further comprises:

A module for visualizing said gaze point in the frames of a video sequence, said module comprising:

a module for determining a point transfer mapping from points of said reference image to corresponding points in the video frames of said video sequence;

a module for using said point transfer mapping to map a gaze point from said reference image to the corresponding point into the corresponding points of the frames of a video sequence.

This enables the visualization of the gaze pint in a video sequence.

According to one embodiment the apparatus further comprises:

A module for mapping the gaze point of a user as detected in a scene image taken by a first camera into the corresponding location in a corresponding frame of a video as taken by a second camera from a different position than said first camera.

This enables the visualization in a video sequence taken from a different position than the scene images.

According to one embodiment the apparatus further comprises:

An eye tracking module for tracking the gaze of a subject; and/or

A head-mounted camera for taking a scene image; and/or

A calibration module for mapping a gaze point to a corresponding point in the scene taken by said head-mounted camera.

This enables the implementation of a complete system comprising eye tracker, calibration module and scene camera.

According to one embodiment there is provided a method for mapping a gaze point of a subject on a scene image to a gaze point in a reference image, wherein said scene image and said reference image have been taken by a camera from a different position, said method comprising:

executing a feature detection algorithm on said reference image to identify a plurality of characteristic features and their locations in said reference image;

executing said feature detection algorithm said scene image to re-identify said plurality of characteristic features and their locations in said scene image;

determining a point transfer mapping that transforms point positions between said scene image and said reference image based on the locations of said plurality of characteristic features detected in said reference image and said scene image;

using said point transfer mapping to map a gaze point which has been determined in said scene image to its corresponding point in said reference image.

In this way a method according to an embodiment of the invention may be implemented.

The method may further comprise the steps as executed by the additional features of one of the other embodiments.

According to one embodiment there is provided a computer program comprising computer program code which when being executed on a computer enables said computer to carry out a method according to one of the embodiments of the invention.

DETAILED DESCRIPTION

Figure 1:
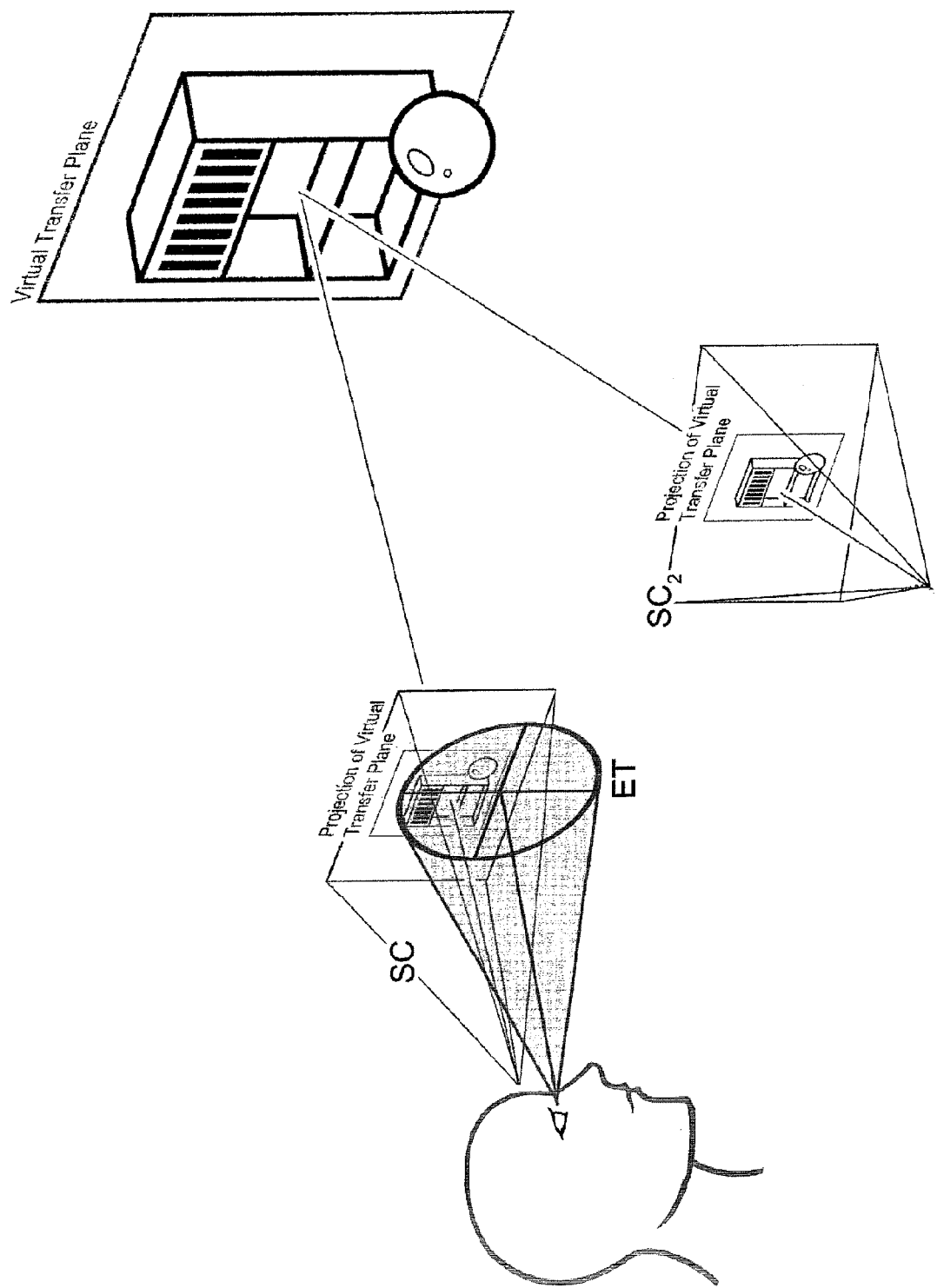
FIG. 1 schematically illustrates the mapping of a gaze point according to an embodiment of the invention.

According to one embodiment there is provided a method and an apparatus which allows mapping the gaze point from a scene image onto a reference image taken from a different position.

For that purpose there is made use of a set of characteristic features (reference features) in the reference image.

According to one embodiment these characteristic features are identified by some feature detection algorithm which is capable of searching for identifiable features in the reference image. According to one embodiment the feature detection algorithm is chosen such that it is capable to re-identify detected features also in a later taken image which is taken from a different position. Using a feature detection algorithm the characteristic features such as reference points, lines or regions can then be re-identified again in a later taken scene image, even if the scene image was taken from a different position.

Suitable features that can be detected by a feature detection algorithm are for example characteristic points or regions like blobs, edges or corners in the reference image. These points or regions which can serve as characteristic features may then be identified by an image processing algorithm which is capable of feature detection in an image taken by a camera, and using such a feature detection algorithm they can then later be re-identified in an image taken by the camera from a different position.

It should be noted that the use of a feature detection algorithm which can process an image to detect one or more characteristic features makes it unnecessary to use an artificial marker such as IR sources and additional detectors such as IR line detectors. Instead, the image itself of a natural scene taken by a camera, without any artificial components or light sources mounted in the scene and without the need for any additional detectors, can be used to identify reference points for determining the mapping. This can be achieved by applying a feature detection algorithm which detects the location of characteristic features in an (unamended or "natural") scene image without the need for artificial markers as provided by IR sources in the prior art.

According to one embodiment the user may manually select (e.g. by the mouse or any other input means) one or more regions in which the feature detection algorithm should be executed to detect the characteristic features. Such points or regions may be selected manually by a user in a reference image, e.g. by marking them with the mouse by clicking on them or by defining an area such as a rectangle or a circle surrounding them to define one or more "areas of interest" on which the feature detection algorithm is executed.

The characteristic features which are then detected with their corresponding location in such an area of interest by the execution of the feature detection algorithm are then detected again in a later image taken by the head-mounted scene camera from a different position, a so-called "scene image", by re-identifying the characteristic features in the scene image as will be described further below. Together the detected characteristic features in the reference image and the re-identified characteristic features in a scene image can be used to determine a point transfer mapping that transforms point positions between the scene image and the reference image. One possible embodiment of such a mapping is a planar homography which can be estimated from the feature positions in the reference image and scene image and transfers point positions via a virtual transfer plane in the world scene from the scene image to the reference image.

The reference image which is taken before the actual measurement sequence consists of a projection of a real world scene onto the image plane of the camera. A scene image which is taken later from a different position of the camera consists of a different projection of the real world scene onto the image plane of the camera which is then located at a different position. However, the mapping between points from a scene image to the corresponding points of a reference image can be determined if a plurality of characteristic features (at least three or more) are identified first in the reference image and then later re-identified in the scene image. The transform which gives this mapping can then be used to map the gaze point from the scene image into its corresponding point in the reference image.

At first, however, the setup procedure during which the characteristic reference features are obtained and a corresponding calibration mechanism according to one embodiment will be described. First, a reference image is taken before the actual measurement sequence (the sequence in which the "scene images" from different positions are taken and the gaze directions are determined). It is used during calibration of the eye tracker to calibrate the correspondence between a gaze direction as detected by the eye tracker and its corresponding point in the reference image as taken by the scene camera. In this manner the calibration of the gaze direction to the corresponding point in the reference image and thereby also to the corresponding point of the "real world scene" as seen in the reference image can be performed. This corresponds to a conventional calibration which maps the gaze direction to a gaze point in case that the head-mounted scene camera does not move.

If in a later actual measurement the head-mounted scene camera together with the head and the eye moves, the image of the scene camera (the "scene image") changes. Thus the positions of the characteristic features detected in the reference image change accordingly.

In such a scenario, according to one embodiment the gaze point detection is then carried out as follows.

First the characteristic reference features are detected again or "re-identified" in a scene image taken by the head-mounted scene camera from a different position.

For this purpose an image processing algorithm is used that is capable of detecting and matching the characteristic features to the known reference features of the reference image which have been determined during the setup procedure.

The feature detection algorithm which is actually used for detection of the characteristic features in the reference image and for re-identifying them in the scene image taken from a different position may be chosen depending on the type of features which are best suited to the application domain.

For example, if the characteristic features which are detected in the reference image and which are to be re-detected and re-identified in the scene image are corners, then a corner detection algorithm may be used, such as e.g. the Moravec corner detection algorithm, the Harris & Stephens corner detection algorithm, the Plessey corner detection algorithm or others.

Once the characteristic features have been detected or re-identified in a scene image taken from a different position than the reference image, they can be used to estimate a plane projective transformation of points of the scene image to points on the reference image.

This will now be explained in more detail with reference to FIG. 1.

FIG. 1 shows a scenery which comprises a bookshelf. As an initial reference image the scene image is taken by scene camera SC in a first position (the "reference position") and is thereby projected onto the image plane of the scene camera SC. As can be seen, the scenery comprises a bookshelf and is projected into the image plane of the scene camera SC when the image is taken.

During a setup procedure a set of characteristic reference features is defined by detecting characteristic features in the reference image or in a part of it, e.g. inside a region of interest like the rectangle which surrounds the bookshelf. This region may have been selected as a "region of interest" by the user during a calibration procedure for defining the region within which a feature detection algorithm is to be executed to detect characteristic features. The region of interest may e.g. be selected by using the mouse to thereby select in the reference image taken by scene camera SC the rectangle which surrounds the bookshelf.

Another possibility of defining the set of characteristic reference features would e.g. be to select four points, say, the four front corners of the bookshelf. Such a selection of the four corner points (e.g., by the mouse) could then according to this embodiment correspond to the selection of a small (predefined) area around the selected point which was selected by the mouse click, and within this area the feature detection algorithm would then be executed to determine the features and their location (within the predefined area surrounding the point selected by the mouse click) by the feature detection algorithm. In this manner the definition of characteristic reference features is carried out by a combination of manual selection (for selecting the points of interest by the mouse click, e.g. the corners of the bookshelf) and automatic detection by executing the feature detection algorithm (within the predefined area around the point selected by the mouse click).

According to another embodiment the whole reference image may form the "region of interest" within which the characteristic features are detected using a feature detection algorithm. Then a Region of interest" like the one indicated by the rectangle surrounding the bookshelf in FIG. 1 is not necessary. In a preferable embodiment, however, the selection of at least one shape or area or region of interest which by its content and by constraining a feature detection algorithm defines the characteristic reference feature set.

With this reference image (or any other image suitable for gaze calibration) then a the calibration of the gaze direction can be performed in a conventional way, which means that there is performed a mapping between the gaze direction as determined by the eye tracker ET and the corresponding gaze point in the reference image. This can e.g. be done by having the subject looking at defined points in the reference image (or any other image suitable for gaze calibration) and determining the corresponding gaze direction as measured by the eye tracker. Based on this data a correspondence between gaze direction determined by the eye tracker and the corresponding gaze point in the reference image (and thereby in the image of the real scenery) can be determined. This calibration is performed while the head-mounted scene camera is at a fixed location and does not move, as in the conventional calibration procedure.

With this calibration the gaze point could then be detected in a conventional way over time by detecting the gaze direction as long as the head-mounted camera does not move.

However, if the head-mounted camera moves, then the scene image taken by the head-mounted scene camera changes, as e.g. shown by the scene image in the image plane of the scene camera SC2 now located at a different position, as can be seen in FIG. 1.

According to one embodiment there is now detected the characteristic reference features which have been defined before (e.g. by the feature detection algorithm executed on the area defined by the rectangle surrounding the bookshelf) in the later taken scene image. For that purpose there is used an image processing algorithm which is capable of—at least partly—re-identifying the previously defined characteristic features (or objects) of the reference image in a subsequent scene image taken from a different position of the head-mounted scene camera.

One suitable algorithm which can be used for this purpose is the so-called scale invariant feature transform (SIFT). With this algorithm feature of objects are first extracted from one or more reference images (e.g. the "reference image" mentioned before) and stored in a database. The features are defined by a location in the image and a feature-descriptor-vector that captures information of the image area surrounding the location in a way that features become comparable by distances of descriptor-vectors. An object is then recognized in a new image by individually comparing each feature from the new image to this database and find candidate matching features based on the Euclidean distance of their feature vectors. From the full set of matches, subsets of features that agree on the object and its location, scale and orientation in the new image are identified to filter out good matches. Each cluster of 4 or more features that agree on an object and its pose is then subject to further detailed model verification and subsequently outliers are discarded. Finally the probability that a particular set of features indicates the presence of an object is computed, given the accuracy of fit and number of probable false matches. Object or feature matches that pass all these tests can be identified as correct with high confidence.

A more detailed description of the SIFT algorithm can e.g. be found in U.S. Pat. No. 6,711,293.

Using the SIFT algorithm it is possible to re-identify or recognize characteristic reference features in the image SC2 shown in FIG. 1.

Therefore, even if the head mounted camera has moved it is possible to determine a mapping that identifies which point in the reference image SC corresponds to a certain point in the scene image taken by SC2. For that purpose there is determined a planar homography between the characteristic features of the reference image and the re-identified characteristic features in the scene image as the mapping, e.g. by using a robust estimator like RANSAC that estimates the planar homography from some or all matched features, discarding outliers that lie too far from an implicitly represented virtual transfer plane. The plane is in most cases an average plane of the scene object points that correspond to the characteristic features as shown in FIG. 1.

This mapping can then be used to map the gaze direction to a gaze point in the reference image. Based on the determination of the gaze direction it is possible to determine the actual gaze point first in the scene image (based on the initial calibration) and then the corresponding point in the reference image (based on the planar homography). This is also illustrated in FIG. 1 and will now be explained in more detail below.

The detection of a certain gaze direction corresponds to a certain point in the later taken scene image SC2, as is illustrated by the line which crosses the image plane in the image taken by camera SC2. This correspondence has been obtained during the calibration through which there has been obtained a mapping of the gaze direction to a point in the scene image as has been explained before in connection with the calibration procedure. This point in the scene image plane which is identified by the gaze direction now corresponds to a certain point of the virtual transfer plane in FIG. 1 as can be seen from FIG. 1, and this point of the virtual transfer plane in FIG. 1 taken by camera SC2 at a different position again corresponds to a certain point in the reference image taken by camera SC in the initial position during calibration. The mapping is given by the planar homography which has been determined to map points of the scene image SC2 to the reference image SC and which has been determined based on the recognition or re-identification of the characteristic features and preferably a robust estimation.

As can be seen from the above description, according to one embodiment there is used a set of characteristic features (such as points, corners or edges) which are identified in the reference image and which together with the re-identified features in a scene image defines a "virtual transfer plane". Camera images are projections of this virtual transfer plane into the image plane of the camera, which leads to different position of the characteristic features in different camera images if they are taken from different camera positions. This virtual transfer plane may be regarded as a "scene stable plane" in the sense that even if the scene image changes due to movement of the camera, it can be "re-identified" in the later taken scene image by re-identifying the characteristic features in a later taken scene image which was taken from a different position by the head-mounted camera. There is used image processing of the images of the head mounted scene camera to first define the characteristic reference features and then again find or re-identify the characteristic features in a later scene image by feature detection instead of resorting to artificial IR light sources which have to be mounted in the real world scenery. Instead a "natural" and unamended image of the real world scenery taken by a normal camera can be used without any artificial markers and without any additional IR detectors, and the gaze point determination can be carried out without resorting to any external markers. Instead the gaze point detection can be performed based on the unchanged scene images alone without any artificial additions, even if the head-mounted camera moves.

The definition of the set of characteristic reference features in the above example has been carried out by selecting a rectangle which surrounds the bookshelf as a "characteristic region" or "region of interest which defines the features contained in it and identified by a feature detection algorithm, as illustrated in FIG. 1.

However, any other regions of interest of reference image which contain characteristic features which are suitable to be re-identified in a later scene image may be chosen as well. For example, one may chose the four front corners of the bookshelf as characteristic points by selecting them with the mouse to thereby define an area of interest around them which is used for executing the feature detection algorithm which in such a case may e.g. be a corner detection algorithm. Such corners may then be re-identified in a later scene image again by a suitable corner detection algorithm such as e.g. the Moravec corner detection algorithm, the Harris & Stephens corner detection algorithm, the Plessey corner detection algorithm or others, which are known to the person skilled in the art.

Moreover, the already mentioned SIFT algorithm mentioned in a foregoing example may also be used.

Another algorithm for feature identification and feature recognition which may be used (based on the reference image as a whole or based on one or more regions of interest defined in the reference image) instead of the SIFT algorithm or in combination with it is the so-called "speeded up robust features" (SURF) algorithm. SURF is based on sums of approximated 2D Haar Wavelet responses around the feature location as feature-descriptor and makes an efficient use of integral images.

It uses an integer approximation to the determinant of Hessian Blob detector to find the feature-location, which can be computed very fast with an integral image. A description of this algorithm can be found e.g. in Herbert Bay, Andreas Ess, Tinne Tuytelaars, Luc Van Gool SURF: "Speeded Up Robust Features", Computer Vision and Image Understanding (CVIU), Vol. 110, No. 3, pp. 346-359, 2008.

As a feature detection algorithm any image processing algorithm may be used which is capable of detecting characteristic features such as points, blobs or regions or objects in a reference image, and which further is capable of recognizing or re-identifying these characteristic features which have been detected in the reference image also in a later taken scene image even if the scene image was taken from a different position. The image processing algorithm should be capable of such a feature detection based on a "natural" image taken by a conventional camera. This avoids the necessity of artificial IR light sources and the need for additional detectors. Instead the feature detection algorithm is chosen such that it can detect inherent characteristic features in any "natural" scene image taken by a normal camera as long as the scene image has a certain contrast and is not completely uniform but contains shapes and contours. By using such a feature detection algorithm the gaze point mapping approach of the embodiments of the invention can in principle be performed based on any scene images without artificially enriching the scene or the scene images by IR light sources. There are a multitude of image processing algorithms which are capable of fulfilling such a function, rather simple ones like corner detection algorithms, and rather sophisticated ones like a SIFT algorithm or a SURF algorithm. All these algorithms have in common that they can operate on natural images without the need for additional IR sources and additional IR detectors, because they can detect and use inherent characteristic features of the images which do not contain artificial IR sources as markers.

According to one embodiment the determination of such characteristic features is done automatically by a feature detection algorithm but may be supported manually, e.g., by selecting (e.g., by the mouse or any input or selection device) a region of interest for executing thereon the feature detection algorithm as described before.

According to one embodiment, however, the characteristic features such as characteristic points or blobs or regions can also be done fully automatically based on the reference image. For example, the SIFT algorithm mentioned before is capable of identifying characteristic points (or features), so called "keypoints" which are then later re-identified in a later image. After having selected the rectangle shown in FIG. 1, the SIFT algorithm therefore may automatically identify the "keypoints" within this rectangle. A fully automatic procedure may be obtained if instead of selecting a rectangle as described before, the whole reference image forms the basis for the feature identification by the SIFT algorithm to define the virtual transfer plane.

To summarize the foregoing description of embodiments, a mapping of the gaze direction of an eye to a reference image of a scene may be performed as follows.

First there is mapped the gaze from the eye tracker ET to the scene camera reference image SC using standard procedures.

Then there is defined a set of characteristic reference features in the reference image by using a feature detection algorithm.

Then there is found the position of the characteristic reference features in any other scene camera image SC2 taken from a different position.

Then there is obtained/calculated the transformation (which is a planar homography) of the scene plane to the virtual transfer plane. Using this transformation a gaze direction (and its corresponding point in the scene image as obtained from a calibration procedure) can be mapped to the corresponding gaze point in the reference image.

It should be noted that the other scene images can not only be from other positions and other times but can even be from other participants (i.e. other persons wearing the head-mounted camera and the eye tracker). It is not necessary to perform a new calibration (i.e. generate a new reference image or features thereon) even if the head-mounted camera is in a subsequent measurement sequence worn by a different subject.

In such a manner a gaze direction can be mapped onto corresponding gaze points on the reference image over time (and even over different participants) so that the gaze point can be recorded over time, even if the head of the user moves and even for different users.

Once the mapping of the gaze to the reference image has been obtained, the gaze may be displayed in the reference image, e.g. by highlighting the location at which the user's gaze was directed, or by displaying a symbol like a cross or any mark at the location of the gaze. If the measurement was conducted over a certain time period, then the corresponding evolution of the gaze point may be displayed by a moving mark or symbol which is shown in the reference image. This is then a visualization of the subject's gaze in the reference image.

However, the initial reference image may possibly not be the best image for such visualization. E.g., if the initial reference image may contain a bookshelf not in a front view but in a perspective view, as shown in FIG. 1. For visualization of the gaze of the subject, however, it may be more desirable to use an image which shows the gaze point in an image which shows a front view of the bookshelf rather than showing it in a perspective view.

For that purpose according to one embodiment one may generate a "final reference image" or a "visualization image" which offers the "desired view" of the scene for which the gaze points are to be determined and tracked.

For the purpose of generating such a "final reference image" one may choose, e.g., a suitable scene image which shows the scene in the desired view. For this scene image, the homography that gives the mapping between the initial reference image and the scene image has already been determined during the actual measurement phase.

This transformation may then be used to map all the gaze points from the initial reference image to the "final reference image" or the "visualization image" that corresponds to the selected scene image.

If no scene image shows the scene in the most desirable manner, one may also take an "external" or "additional" image of the scene as a final reference image, possibly even by a different camera, e.g. with a higher resolution and from the desired perspective. In this final reference image then there is performed the feature detection algorithm to detect or re-identify the characteristic reference features. Based on the recognized features one may then again determine the corresponding transformation from the initial reference image to the final reference image (the visualization image), and using the thus determined transformation the detected gaze points in the initial reference image may be transformed or mapped onto the visualization image.

According to one embodiment the final reference image is generated such that it shows the scene image best in such a way that the gaze points when transformed onto the final reference image are presented in the most desirable way. This is e.g. the case if the objects on which the gaze point is to be determined are shown in a front view rather than in a perspective view, or if the final reference image is larger or has a better resolution than the scene images.

Figure 2:
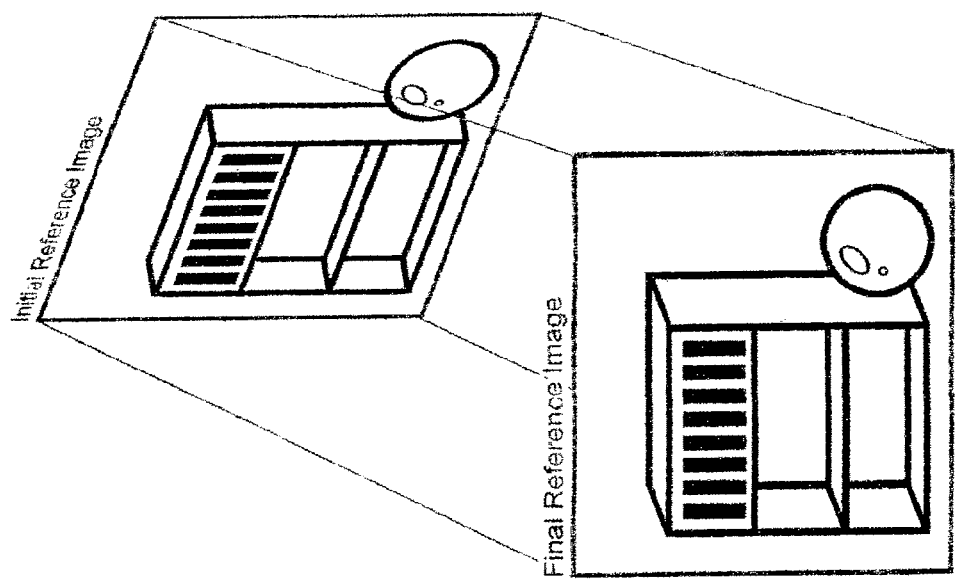
FIG. 2 schematically illustrates the mapping of an initial reference image to a final reference image according to an embodiment of the invention.

An example of the case where the final reference image is geometrically modified compared to the initial reference image in order to offer a more frontal view of the scene than the initial reference image is schematically illustrated in FIG. 2. FIG. 2 shows the initial reference image of FIG. 1 and a final reference image which offers a more front view than the initial reference image. Also schematically illustrated is the projection which projects the initial reference image onto the final reference image and which corresponds to the homography or transformation which is determined to obtain the mapping. Another example of a geometric modification would be a change of the aspect ration of the image.

According to a further embodiment the final reference image may be obtained by removing distortions from the initial reference image, for example by removing camera distortions such as barrel distortions.

According to one embodiment the generation of the final reference image or visualization image may comprise the stitching of images. It also may comprise the rectification of one or more scene images or their stylization, e.g. by marking certain areas or parts, or sketching a stylized drawing. The visualization image may in one embodiment even be a handmade drawing.

Depending on the kind of image used as visualization image there may be used different methods to determine the point transfer mapping from the reference image to the visualization image. If e.g. the visualization image was taken with the same camera as the reference image, then the feature detection algorithm which has already been described may be used for that purpose.

If, however, the visualization image is a stylized image or even a sketch or a handmade drawing, then the point transfer mapping may be defined manually, e.g. by mapping triangles or even point by point.

According to one embodiment the visualization of the mapped gaze point is not made in a single visualization image but in the frames of a video sequence which act as a sequence of visualization images.

For that purpose there is determined a point transfer mapping between the reference image and each frame of the video sequence, and this mapping can then be used to map the gaze point of one or more users over time into the frames of a video sequence. In this manner the gaze point taken and recorded over time by a head-mounted video camera can be mapped via the reference image into another video taken by a different camera from a different position or perspective. The gaze of one or more users as it evolves over time can in this way be mapped into the same video of the scene possibly taken from a different and more desirable perspective.

Once the final reference image has been generated the feature detection algorithm can be executed on it to detect therein the characteristic reference features. By calculating then the homography between the features a mapping of the gaze points to the final reference image can be obtained. Any other means of determining a mapping that can transform points from the initial reference image to their corresponding location on the final reference image can also be used e.g. defining a homography by hand (e.g. by specifying 4 point matches) or e.g. even defining the transformation point by point.

As has been described before in relation to other embodiments, for automatic image processing to detect the characteristic features the image part for the feature detection to work on can be characterized by the content of an area (a region of interest), the content of that area thereby defining the region within which the algorithm looks for the characteristic features or the objects which can be identified in that content of the area of interest. A homography is calculated from characteristic reference features in another scene image and characteristic reference features in the reference image which define an implicit virtual scene plane that facilitates the point transfer. The homography transforms all points of the scene image (which corresponds to the points of a virtual transfer plane in the real world scene and all and points off the plane with parallax error relative to their distance from the plane) to points on the reference image and in extension to any reference image thus reducing the mapping of points for a moving person with a head-mounted eye tracker to the case of a fixed eye tracker. Therefore the gaze point tracking can be performed even if the head-mounted camera moves.

According to one embodiment, by defining a certain object (or one or more objects) in the reference image through their shape or contour (e.g. through their boundaries) one can compare for a certain gaze point whether this gaze point lies within such a boundary of an object or not. If yes, then it can be determined that the gaze rests on the corresponding object, and if not it does not.

The identification as to whether the gaze rests on a certain object or not is made based on the gaze mapped onto the reference image instead of based on the gaze determined in the scene images. Substituting all scene images by one reference image and mapping the gaze onto it (possibly even from different participants and times) makes it possible to visualize and do statistics on aggregated gaze data. Analysis of head-mounted eye tracker data (at least for the gaze data on the virtual transfer plane) thereby becomes the same as analyzing eye tracking data with a fixed head.

It will be understood by a person skilled in the art, that the embodiments described hereinbefore may be implemented by hardware, by software, or by a combination of software and hardware. The modules and functions described in connection with embodiments of the invention may be as a whole or in part implemented by microprocessors or computers which are suitably programmed such as to act in accordance with the methods explained in connection with embodiments of the invention. This may involve the connection of such computers or microprocessors with suitable interfaces and/or measuring devices as they are used in the field of eye tracking and image processing, as will be readily understood by the skilled person.

The invention claimed is:

1. An apparatus for mapping a gaze point on a scene image to a corresponding point in a reference image, wherein said scene image and said reference image have been captured from different positions and orientations by a head-mounted camera which can change position and orientation due to movement by a subject, said apparatus comprising:
   a head-mounted camera for taking said scene image;
   an eye tracker that determines a direction of the subject's gaze and maps the gaze direction onto said scene image;
   processing means for:
      identifying a plurality of characteristic features and their locations in said reference image;
      re-identifying said plurality of characteristic features and their locations in said scene image;
      determining a point transfer mapping that transforms point positions between said scene image and said reference image based on the locations of said plurality of characteristic features detected in said reference image and said scene image; and
      using said point transfer mapping to map a gaze point which has been determined in said scene image to its corresponding point in said reference image.

2. The apparatus of claim 1, wherein
   said point transfer mapping is a planar homography which is estimated from the features in the reference image and scene image and transfers point positions via a virtual transfer plane in the world scene from said scene image to said reference image.

3. The apparatus of claim 1, further comprising:
   means for determining one or more regions of interest in said reference image within which said feature detection algorithm is executed to detect and locate said characteristic features therein.

4. The apparatus of claim 1, wherein said processing means executes at least one of the following:
   a scale invariant feature transform algorithm;
   a speeded up robust features algorithm.

5. The apparatus of claim 1, further comprising:
   means for mapping the gaze points from different persons and/or different times in different scene images to corresponding points in the reference image and for recording the mapped gaze points over time.

6. The apparatus of claim 1, further comprising:
   means for displaying said mapped gaze point in said reference image as its location evolves over time.

7. The apparatus of claim 1, further comprising:
   means for visualizing said mapped gaze point in a visualization image different from said reference image, said means comprising:
   means for determining a point transfer mapping for transferring a point from said reference image to said visualization image;
   means for using said point transfer mapping to remap said mapped gaze point from said reference image to its corresponding point in said visualization image; and
   means for displaying said remapped gaze point in said visualization image.

8. The apparatus of claim 7, wherein
   said processing means determines said point transfer mapping based on characteristic features which have been detected in said reference image and which have been detected and re-identified in said visualization image.

9. The apparatus of claim 7, wherein said visualization image is one of the following:
   an image selected from scene images taken from different positions;
   an image generated by stitching two or more of the scene images taken from different positions;
   a geometrically modified image of the scene;

an image of the scene from which distortions have been removed;

an external image taken by a different camera;

an image taken at a time different from the actual measurement of the gaze points;

an image having a higher resolution than said reference image;

a cartoon or a sketch;

a stylized drawing a handmade drawing.

10. The apparatus according claim 1, further comprising:

means for visualizing said mapped gaze point in the frames of a video sequence, said module comprising:

means for determining a point transfer mapping from points of said reference image to corresponding points in the video frames of said video sequence; and means for using said point transfer mapping to remap a mapped gaze point from said reference image into the corresponding points of the frames of a video sequence.

11. The apparatus of claim 10, further comprising:

means for mapping the gaze point of a user as detected in a scene image taken by a first camera into the corresponding location in a corresponding frame of a video as taken by a second camera from different positions than said first camera.

12. A method for mapping a gaze point of a subject on a scene image to a corresponding point in a reference image, wherein said scene image and said reference image have been taken from different positions and orientations by a head-mounted camera which can change in position and orientation due to the movement of the subject, said method comprising:

tracking the gaze of said subject by an eye tracker;

taking said scene image by a head-mounted camera;

mapping a gaze point to a corresponding point in said scene image taken by said head-mounted camera, said method further comprising:

executing a feature detection algorithm on said reference image to identify a plurality of characteristic features and their locations in said reference image;

executing said feature detection algorithm said scene image to re-identify said plurality of characteristic features and their locations in said scene image;

determining a point transfer mapping that transforms point positions between said scene image and said reference image based on the locations of said plurality of characteristic features detected in said reference image and said scene image;

using said point transfer mapping to map a gaze point which has been determined in said scene image to its corresponding point in said reference image.

13. A non-transitory computer readable medium having recorded or embodied thereon computer program code which when being executed on a computer enables said computer to carry out a method according to claim 12.

14. The apparatus of claim 1, further comprising:

means for defining object boundaries for one or more objects in the reference image; and means for determining whether a mapped gaze point in the reference image, which corresponds to a gaze point in the scene image, lies within an object boundary.

15. The method of claim 12, further comprising:

defining object boundaries for one or more objects in the reference image; and determining whether a mapped gaze point in the reference image, which corresponds to a gaze point in the scene image, lies within an object boundary.

* * * * *